(12) United States Patent
Okamoto et al.

(10) Patent No.: US 6,569,671 B1
(45) Date of Patent: May 27, 2003

(54) PATTERN EXPOSURE METHOD, EXPOSURE DEVICE, FORMATION OF NUCLEIC ACID ARRAY, AND FORMATION OF PEPTIDE ARRAY

(75) Inventors: Tadashi Okamoto, Yokohama (JP); Nobuko Yamamoto, Isehara (JP); Tomohiro Suzuki, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/764,422

(22) Filed: Jan. 19, 2001

(51) Int. Cl.[7] .............................. C12M 1/00; C12Q 1/68; C12P 19/34; C07H 21/02; C07H 21/04
(52) U.S. Cl. .................... 435/285.1; 435/6; 435/7.1; 435/91.1; 435/91.2; 435/283.1; 435/287.2; 536/22.1; 536/23.1; 536/24.3; 536/24.31; 536/24.32; 536/24.33; 359/618; 359/628; 355/344
(58) Field of Search ............................ 435/6, 7.1, 91.1, 435/91.2, 287.2, 174; 536/22.1, 23.1, 24.3–24.33; 359/618, 626

(56) References Cited

U.S. PATENT DOCUMENTS

| | | | |
|---|---|---|---|
| 5,202,231 A | | 4/1993 | Drmanac et al. ............... 435/6 |
| 5,424,186 A | | 6/1995 | Fodor et al. .................... 435/6 |
| 5,445,934 A | | 8/1995 | Fodor et al. .................... 435/6 |
| 5,936,730 A | * | 8/1999 | Foley et al. ................. 356/344 |
| 6,252,715 B1 | * | 6/2001 | Rope et al. .................. 359/618 |
| 6,353,502 B1 | * | 3/2002 | Marchant et al. ........... 359/626 |
| 6,424,418 B2 | * | 7/2002 | Kawabata et al. .......... 356/445 |

FOREIGN PATENT DOCUMENTS

| | | |
|---|---|---|
| JP | 5-167192 | 7/1993 |
| JP | 6-237043 | 8/1994 |
| WO | WO 89/10977 | 11/1989 |

OTHER PUBLICATIONS

Hayashi, et al; "Record Low–Threshold Index–Guided InGaAs/GaAIAs Vertical–Cavity Surface–Emitting Laser With A Native Oxide Confinement Structure", Elec. Letters vol. 31, No. 7 (1995) 560–562.

Babić, et al; "Double–Fused 1.52–$\mu$m Vertical–Cavity Lasers", Appl. Phys. Lett. vol. 66, No. 9 (1995) 1030–1032.

* cited by examiner

*Primary Examiner*—Jeffrey Siew
(74) *Attorney, Agent, or Firm*—Fitzpatrick, Cella, Harper & Scinto

(57) ABSTRACT

This invention provides a pattern exposure method which may be used for effectively preparing, for example, a DNA or peptide array with a lower cost and a device therefor. Specifically, the method is a method for pattern exposure comprising the step of exposing a photosensitive material on a solid-phase substrate by irradiating it with a light as a pattern, wherein the photosensitive material is selectively exposed with beams selectively emitted from multiple vertical cavity surface emitting laser sources aligned as an array.

3 Claims, 2 Drawing Sheets

25.4mm 25.4mm

25 μm

PATTERN EXPOSURE METHOD, EXPOSURE DEVICE, FORMATION OF NUCLEIC ACID ARRAY, AND FORMATION OF PEPTIDE ARRAY

BACKGROUND OF THE INVENTION

1. Field of the Invention

This invention relates to an exposure method for conducting a process on a solid substrate using exposure, a process for sequential extension and/or preparation of a nucleic acid or peptide using the exposure method and an exposure device for conducting the exposure method.

2. Related Background Art

Recently, so-called sequencing by hybridization (SBH), in which hybridization of multiple nucleic acid probes is used to determine a base sequence in a particular target nucleic acid, has been intensely investigated. For example, U.S. Pat. No. 5,202,231 has disclosed the principle of SBH. EP Patent Publication 0373203 B1 has described an SBH method and a device using a solid-phase DNA array. Furthermore, U.S. Pat. No. 5,445,934 has described a stepwise process for preparing a nucleic acid combining a photolytic protective group and photolithography as a method for forming a two-dimensional DNA array on a solid-phase substrate.

Chemical synthesis of a nucleic acid has recently become a popular technique, and a DNA synthesizer has been marketed from several companies. There are several known methods for preparing a nucleic acid, among which a phosphoramidite method is most typical. The phosphoramidite method sequentially extends/synthesizes nucleotides at 5' terminal side starting from a nucleotide with desired bases bound to a solid-phase substrate such as glass beads at its 3' terminal. In the process, hydroxy group at the 5' terminal of a synthesized nucleic acid strand is protected with a protective group such as dimethoxytrityl, which is then removed lust before reaction for introducing a next nucleotide. Generally, this protective group is removed under the acidic condition. The above process in U.S. Pat. No. 5,445,934 is basically an application of the sequential synthesis of a nucleic acid on a solid-phase substrate, but the above method for removing a protective group under the acidic condition is not suitable for synthesizing multiple different nucleic acid strands in a two-dimensional array because one range (matrix) forming a two-dimensional array has a size of several ten $\mu$m to several hundred $\mu$m and the number of matrices, i.e., types of nucleic acid strands, is several hundreds to several millions. It is basically difficult to individually place these many small regions under the acidic condition for deprotection. Thus, the above U.S. Pat. No. 5,445,934 uses a substrate to which a photolytic protective group (strictly speaking herein, a functional group) is attached via a linker as a starting material. First, a protective group at a position to which the first base (one of A, T, G and C) is to be introduced is removed according to the principle of photolithography, i.e., by partial exposure using a photomask to introduce a desired nucleotide, where hydroxyl group at 5' terminal in the first nucleotide is similarly protected by a photolytic protective group. This procedure is repeated four times to introduce all the first nucleotides. Then, the second nucleotides are similarly introduced. The above procedure is repeated 4×N times (N is the length of the nucleic acid strand) in total to provide a nucleic acid strand with a desired length. The number of the type of prepared nucleic acid and the overall size of the formed DNA array depend on the size of the substrate used and the pattern of the photomask used, basically allowing us to prepare a two-dimensional DNA array with a similar fineness to that achieved in a semiconductor process. U.S. Pat. Nos. 5,445,934 and 5,424,186 have described in detail a photolytic protective group which may be used in such a process.

However, preparation of a two-dimensional DNA array using the above photolytic protective group may require 32 to 40 pieces of photomasks even for synthesizing an octamer to decamer nucleic acid which is a minimum requirement as a nucleic acid probe, and the corresponding number of exposure operations and associated steps. Furthermore, for preparing 18-mer to 20-mer nucleic acid representing an adequate length as a DNA probe, 72 to 80 pieces of photomasks are required and steps and a time taken for the process are enormous. Since a photomask is basically a consumable material, increase in the number of photomasks leads to significant increase in a cost.

SUMMARY OF THE INVENTION

In view of the above problems, an objective of this invention is to provide a pattern exposure process and a device which can be used for effectively preparing a DNA array or peptide array with a lower cost.

Another objective of this invention is to provide a method for effectively forming a nucleic acid array and a peptide array.

An embodiment of a method for pattern exposure which can achieve the above objectives is a method for pattern exposure comprising the step of exposing a photosensitive material on a solid-phase substrate by irradiating it with a light as a pattern, wherein the photosensitive material is selectively exposed with beams selectively emitted from multiple vertical cavity surface emitting laser (VCSEL) aligned as an array.

A method for preparing a nucleic acid array which can achieve the above objectives is a method for forming a nucleic acid array where multiple nucleic acid strands attach to multiple positions on a substrate surface and each of the nucleic acid strands has an inherent base sequence, comprising the steps of:

i) preparing a substrate with the surface on which a nucleic acid is bound at multiple positions, in which one end is bound to the substrate while the other end is protected with a photolytic protective group; and ii) selectively irradiating given nucleic acids among the multiple nucleic acids bound to the substrate surface with a light using an exposure device where multiple VCSEL sources are aligned as an array such that each of the photolytic protective group may be irradiated with each beam from the light source to remove the photolytic protective group and then the nucleic acid strand is extended by binding a given nucleotide according to the base sequence.

A method for preparing a peptide array which can achieve the above objectives is a method for forming a peptide array where multiple peptide strands attach to multiple positions on a substrate surface and each of the peptide strands has an inherent sequence, comprising the steps of:

i) preparing a substrate with the surface on which a peptide is bound at multiple positions, in which one end is bound to the substrate while the other end is protected with a photolytic protective group; and ii) selectively irradiating given peptides among the multiple peptides bound to the substrate surface with a light using an exposure device where multiple VCSEL sources are aligned as an array such that each of the photolytic protective group may be irradiated with each emission beam from the light source to remove the photolytic protective group and then the peptide strand is extended by binding a given peptide according to the sequence.

An embodiment of an exposure device which can achieve the above objectives is an exposure device for exposing a photosensitive material on a solid-phase substrate to a patterned beam, wherein multiple VCSEL sources are aligned as an array, and having a configuration such that the photosensitive material can be selectively irradiated with each emission beam from the light source.

This invention employs a VCSEL as a light source for exposure in photolithography for solving the above problems in the prior art. Specifically, in a process requiring exposure on a solid-phase substrate, exposure is conducted by emission, lighting or light showing (hereinafter, collectively referred to as "emission") of each of the multiple VCSEL aligned as a two-dimensional array in a desired pattern by a given procedure. Using such a method, since an exposure pattern may be varied by changing an emission pattern of the surface emitting lasers aligned on the two-dimensional array, necessity of individually changing a photomask for each pattern may be eliminated. In other words, it is not necessary to prepare photomasks corresponding to individual patterns or to change a photomask, resulting in easy exposure operation. Furthermore, since a photomask as a consumable material is not needed, an expense for exposure and a running cost may be reduced. On the other hand, compared with scanning exposure with a laser beam, since the material is exposed as a desired pattern in one time, it may basically eliminate a time for scanning. Furthermore, since a surface emitting laser basically provides a stronger optical power per an area, a time for exposure may also reduced. Additionally, there is another advantage that a program for pattern exposure is considerably simpler and more convenient than that required in laser-beam scanning.

DETAILED DESCRIPTION OF THE PREFERRED EMBODIMENTS

Figure 1:
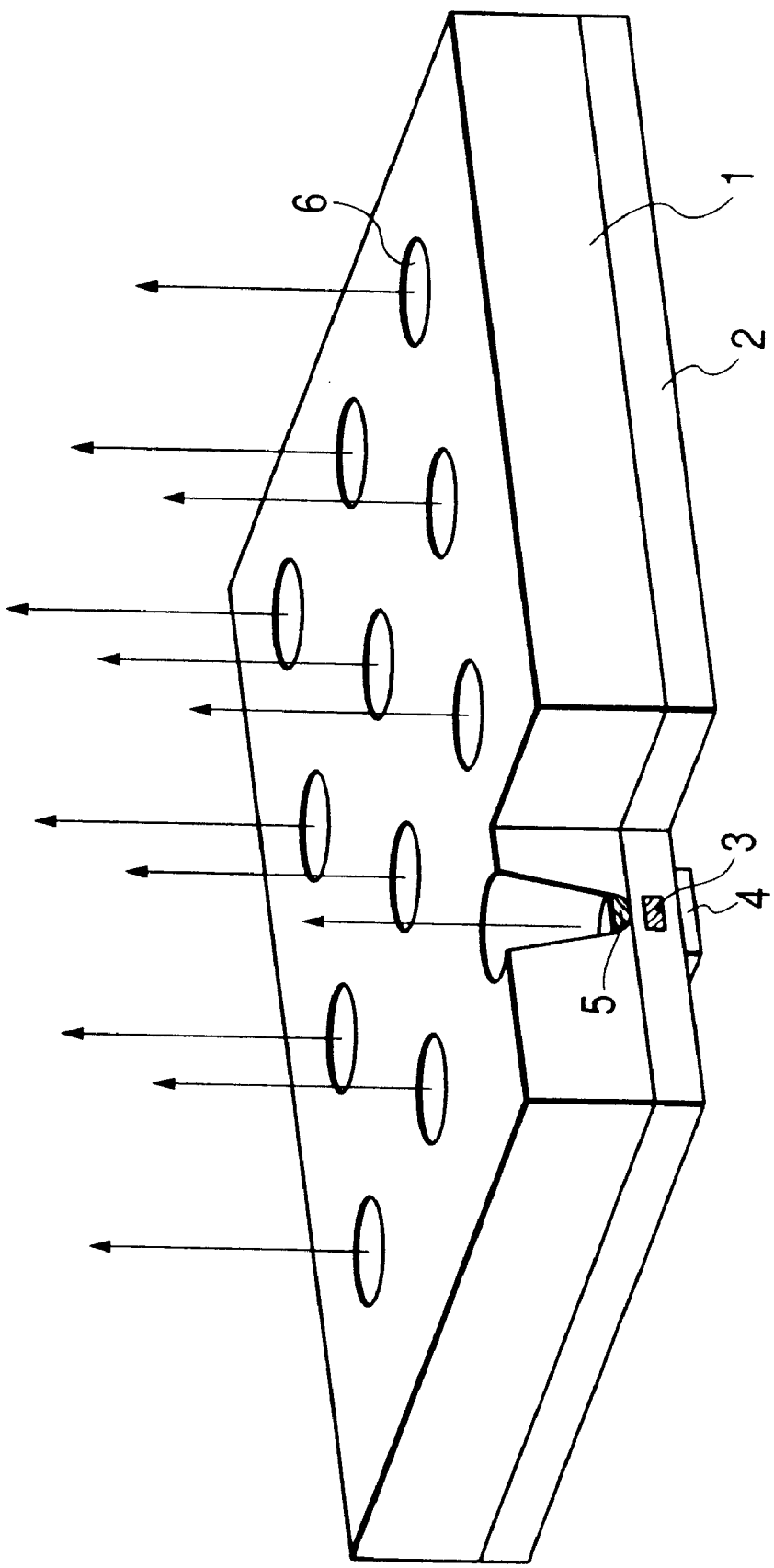
FIG. 1 illustrates the basic structure of a vertical resonator surface emitting laser.

A surface emitting laser with a wavelength from about 350 nm (blue) to 1.55 $\mu$m (communication zone) has been recently investigated with various material systems such as GaN systems on a sapphire substrate; GaAlInP, InGaAs, GaInNAs and GaAlAs systems on a GaAs substrate; and GaInAsP and GaAlInAs systems on an InP substrate. FIG. 1 illustrates the basic structure of a surface emitting laser. An active layer 3 is formed on an epitaxial growth layer 2 (cladding layer) deposited on a semiconductor substrate 1 to a thickness of about several $\mu$m. On both sides of the active layer are formed multilayer dielectric film mirrors 4, 5 with a higher reflectance of 99% or more. A pixel 6 has the appearance of the active layer 3, from which a laser beam is vertically emitted from the substrate. The reflecting films are mainly multilayer films with a thickness of $\lambda/4$ and different refractive indices, and are generally made of a dielectric glass or an epitaxially-grown semiconductor. An epitaxially-grown mirror is described in, for example, Electronics Letters, 31, p.560 (1995) where a multilayer film mirror made of AlAs/GaAs and an active layer are formed on a GaAs substrate in one growth and Applied Physics Letters, 66, p.1030 (1995) where A GaAs/AlAs mirror on a GaAs substrate is adhered by direct lamination to a laser structure made of an InGaAsP/InP system grown on an InP substrate. Alternatively, it may be formed by epitaxial growth from a substrate having an aperture as disclosed in Japanese Patent Application Laid-open Nos. 5-167192 and 06-237043. An emission surface in a laser device has a size of 5 to 30 $\mu$m and has a feature that a beam spreading angle is significantly smaller than that in a gas laser or a usual semiconductor laser. Furthermore, a laser emission surface may be decentered to give a polarized light without using a polarizer. Many surface emitting lasers may be formed as an array on one silicon substrate by applying a processing technique.

A configuration of a surface emitting laser may be, of course, selected depending on the type of a material to be exposed, i.e., factors such as absorbed wavelength properties and sensitivity. A variety of surface emitting lasers covering the above wavelength zone have been developed. Therefore, almost all kinds of materials, for example, in terms of an organic compound can be exposed although exposure is generally conducted using an ultraviolet zone of 400 nm or less in view of previous experience if the material to be exposed is a photoresist. In such a case, for example, a cladding layer may be made of AlGaN (Al composition: 10%); an active layer may be made of GaN; and a reflecting film may be an AlGaN/AlN multilayer film. However, this invention is, of course, not limited to these materials.

Multiple surface emitting laser elements may be, of course, formed on a substrate as a two-dimensional array as described above. These may be, therefore, lighted as a pattern to conduct exposure in a desired pattern. As described above, the size of an emission element in a current surface emitting laser is 5 to 30 $\mu$m which is inferior to a semiconductor level of fineness, but may be an adequate fineness for some photolithography processes. Furthermore, future progress in a process for manufacturing a surface emitting laser itself would probably allow us to conduct exposure using a surface emitting laser with a fineness of 1 $\mu$m or less. Even with a current fineness, optical reduced size projection might be used to improve a fineness.

For the above two-dimensional DNA or peptide array, the size of the emission element of 5 to 30 $\mu$m is appropriate so that the device as such can be used as an exposure device. For example, a two-dimensional DNA array may be easily prepared by using the ultraviolet-emittable surface emitting laser with the above configuration and the photolytic protective group described in U.S. Pat. Nos. 5,445,934 and 5,424,186.

As described above, a beam from each surface emitting laser in this invention has a spreading angle significantly smaller than that from a usual semiconductor laser and in some cases may be used for exposure as it is. In some cases, laser beams may be redirected to be parallel beams or focused using, for example, a microlens adjacent to and facing an emission surface. Here, the microlens may be a microlens array corresponding to a surface emitting laser array.

Even a surface emitting laser has an intensity distribution in an emission surface. Usually, such an intensity distribution is a Gaussian distribution and when a material to be exposed is irradiated with a beam with a lower intensity, the beam may adversely affect the material. In such a case, exposure may be conducted by irradiation from a zone emitting a necessary and sufficient optical quantity for exposure by the use of masking means with a proper aperture diameter.

As described above, in this invention, exposure is conducted by individually lighting multiple VCSEL aligned as an array in a desired pattern by a given procedure, in a process requiring light irradiation on a solid-phase substrate. This process may be a physical process such as thermal deformation of a metal thin film on the substrate surface. Alternatively, it may be, of course, a chemical process as described above.

A chemical process will be further described. When the chemical process is an organic photolytic process or even an organic photopolymerization process, an exposure method of the present invention may be used. Examples of a photolytic process include photolysis of a positive type photoresist, a functional group and a protective group. A photopolymerization process may be, for example, a photopolymerization process of a negative type photoresist. A similar example may be an organic photocoupling process between functional groups.

An example of application of this invention is a method for sequentially extending a nucleic acid or peptide strand by photodegrading or removing a terminal protective group according to a method of the present invention in sequential extension/synthesis of a nucleic acid or peptide as described above.

The present invention encompasses a device allowing us to conduct the above exposure methods. It is specifically a device initiating by exposure a process required on a solid-phase substrate wherein multiple VCSEL aligned as an array are individually emitted lighted, or light-showed in a desired pattern by a given procedure. Examples of a device according to the present invention may be exposure devices wherein individual surface emitting lasers aligned as an array are electrically controlled for controlling ON-OFF of light emission to provide a desired pattern. Alternatively, an emitting beam from a laser may be controlled by an external shutter system. As an example of such a method, when beams from individual lasers are adequately coherent, their polarization property may be used, e.g., liquid-crystal shutters corresponding to individual surface emitting lasers are aligned, to control emission.

EXAMPLES

The present invention will be specifically described with reference to Examples.

Example 1

Figure 2:
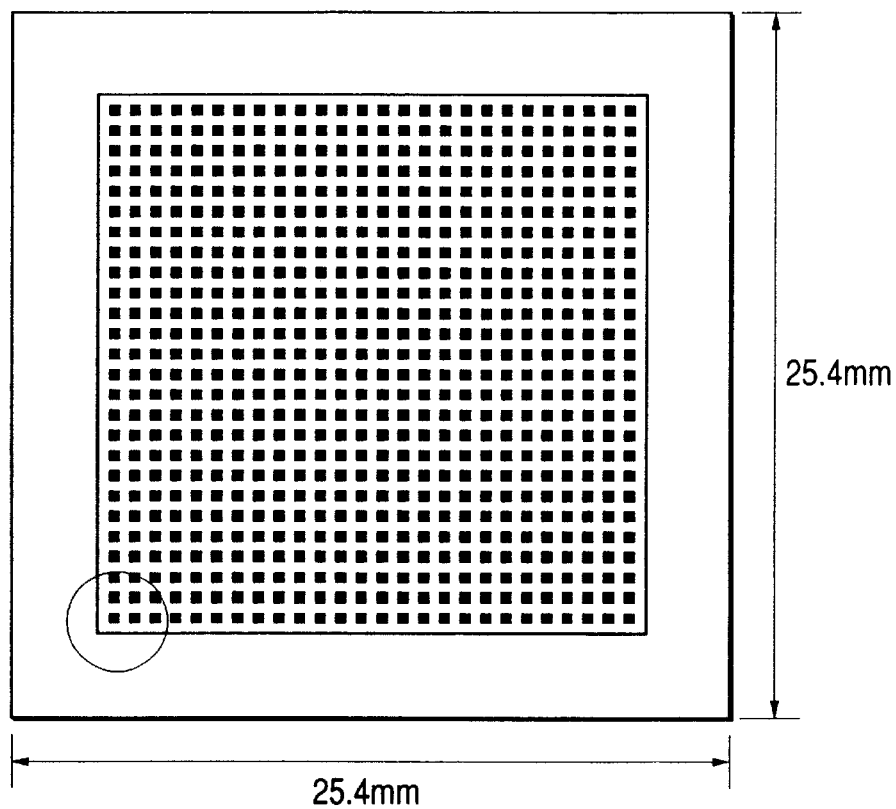
FIG. 2 shows a pattern in a surface emitting laser array.
Figure 3:
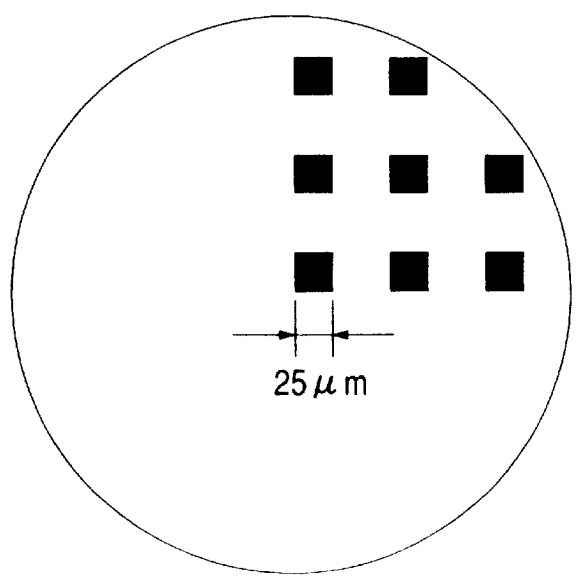
FIG. 3 is a partially enlarged view showing a pattern in a surface emitting laser array.

Preparation of a Two-dimensional DNA Probe Array (Same Sequence) Using a VCSEL Array (1) Preparation of a VCSEL Array As described above was prepared a surface emitting laser array comprising a cladding layer made of AlGaN (Al composition: 10%), an active layer made of GaN and an AlGaN/AlN multilayer film as a reflecting film. The pattern of the array was constituted by 26×26=676 pieces of surface emitting lasers in an area of about 20 mm×20 mm in an square of 25.4 mm×25.4 mm in the light of a DNA probe array pattern described later. Each surface emitting laser had a size of 25 $\mu$m×25 $\mu$m and a distance between lasers was about 50 $\mu$m. This pattern is a typical example and not so significant. FIGS. 2 and 3 are a schematic view of the pattern and a partially enlarged view thereof, respectively.

A wavelength of a beam from the surface emitting laser array formed was 350 nm. The surface emitting lasers were individually connected by wiring for permitting them to be individually lighted.

On the surface emitting laser array was deposited a molded lens array to redirect emitted beams to parallel beams for directly irradiating a reaction vessel with a laser beam during preparation of a solid-phase oligonucleotide later described.

(2) Preparation of a Solid-phase Substrate a) A fused quartz glass substrate with a size of 25.4 mm×25.4 mm and a thickness of 0.5 mm (Iiyama Tokushu Glass Co., Ltd.) was subject to ultrasonic cleaning in an aqueous solution of a detergent for ultrasonic cleaning (BRANSON GP-II) at room temperature for 10 min, washed with water as appropriate, immersed in a 10% aqueous solution of sodium hydroxide at 70° C. for 10 min, washed with water and dried.

b) The substrate was immersed in a 1% solution of bis(2-hydroxyethyl)aminopropyltriethoxysilane in ethanol at room temperature for 2 hours, washed with ethanol, dried under the stream of nitrogen gas and baked at 110° C. for 2 hours.

c) After cooling, the substrate was placed in a custom-made glass reaction vessel with a content of about 0.7 mL which was sealed for preventing liquid from going around to the rear face. In the vessel were added 0.4 mL of a mixed solution of 0.2M monodimethoxytrityl pentaethyleneglycol-β-cyanoethylphosphoramidite and 0.4 M tetrazole in acetonitrile (nucleic acid synthesis grade). The vessel was sealed with a lid and kept at room temperature for 3 min. The substrate was rinsed with acetonitrile and immediately used in synthesis of a solid-phase oligonucleotide.

(3) Preparation of an Oligonucleotide (the Same Sequence, 12-mer of Thymidylic Acid; T12)

a) The above reaction vessel was inserted in a channel in an automated polynucleotide synthesizer (ABI381A), permitting a nucleic acid to be synthesized on the substrate.

b) A program of the automated synthesizer was changed such that deblocking operation was made to be mere washing operation with acetonitrile, and a stop time was taken immediately before the operation for exposure with the above laser array. Exposure was conducted with an exposure energy of about 10 J/cm for 5 sec. An operation time in each step was appropriately adjusted in the light of the content of the above reaction vessel.

c) On a solid-phase substrate was synthesized a 12-mer of thymidylic acid according to a usual procedure except step b), using thymidylic acid phosphoramidite as a nucleotide monomer in which 5'-hydroxy group was protected with 6-nitroveratryl which is a photolytic protective group. An end 5'-terminal hydroxyl was deprotected.

(4) Identification of a Solid-phase Oligonucleotide by Hybridization of a 12-mer of Adenylic Acid (A12)

a) The substrate comprising T12 on its surface was immersed in a 50 mM phosphate buffer (pH 7.0) containing 2% BSA (fetal bovine serum albumin) and 100 mM NaCl at room temperature for 2 hours. The surface was blocked for preventing a dye-labeled oligonucleotide from being non-specifically adsorbed during hybridization later described. Then, the substrate was rinsed with a 50 mM phosphate buffer (pH 7.0) containing 50 mM NaCl.

b) A12 to which rhodamine (TAMRA) was bound via a hexanolamine linker at 5'-terminal (purchased from Nippon Seihun Co. Ltd.) was dissolved in a 50 mM phosphate buffer (pH 7.0) containing 100 mM NaCl to a concentration of 25 nM. The substrate in a) was reacted with the solution placed in the above reaction vessel for hybridization. Without washing the substrate (it had been confirmed that intense fluorescence derived from rhodamine was observed only when there were mutually complementary sequences under these conditions), the substrate was covered with cover glasses to be observed with a fluorescence microscope (Nikon; Eclipse E800, 20x object lens, Filter block; Y-2E/C). Fluorescence corresponding to the pattern of the surface emitting laser array used in deprotection was observed.

Example 2

Preparation of a Two-dimensional DNA Probe Array (Different Sequences) Using a Vertical Resonator Surface Emitting Laser Array (Basically as Described in Example Except that an Oligonucleotide Sequence was Changed)

(1) Synthesis of an Oligonucleotide a) As described in Example 1, in an automatic polynucleotide synthesizer was placed bottles of a solution of phosphoroamidate of adenylic acid, thymidylic acid, cytidylic acid or guanylic acid as a nucleotide monomer, which had a photolytic protective group.

b) By appropriately controlling an emission pattern of the surface emitting laser array, 100 oligonucleotides as a matrix of 10×10 having one of the four different base sequences, which are typical sequences but do not limit this invention, respectively.

SEQ. ID No. 1: 5'ACTGGCCGTCGTTTTACA3'
SEQ. ID No. 2: 5'ACTGGCCGTTGTTTTACA3'
SEQ. ID No. 3: 5'ACTGGCCGTTTTTTTACA3'
SEQ. ID No. 4: 5'ACTGGCATCTTTTTACA3'

To a base sequence of a dye-labeled oligonucleotide used in hybridization later described, SEQ. ID No. 1 is completely complementary and SEQ. ID Nos.2, 3 and 4 are mismatch sequences at marked one, three and six bases, respectively. The base sequence of the dye-labeled oligonucleotide is shown below.

SEQ. ID No. 5: 5'TATAAAACGACGGCCAGT3'

(2) Hybridization a) A rhodamine-labeled oligonucleotide having SEQ. ID No. 5 was hybridized with a substrate comprising one of the four oligonucleotides under the conditions as described in Example 1.

b) By fluorescence microscopy, fluorescence corresponding to the pattern of the surface emitting layer array used for exposure was observed in a region having SEQ. ID No. 1, 2 or 3 whereas fluorescence was not observed in a region having SEQ. ID No. 4. A fluorescence intensity image was taken with a CCD camera equipped with an image intensifier (Hamamatsu Photonics, C2400-87) and quantified as an average per pixel using an image processor (Hamamatsu Photonics, Argusu 50, applied voltage level: 2.0). The results are shown below.

SEQ. ID No. 1: 9650
SEQ. ID No. 2: 4520
SEQ. ID No. 3: 1470
SEQ. ID No. 4: 140
Background: 129

The results indicate that the desired oligonucleotides were synthesized on the substrate and that these were detected by hybridization while difference in mismatch between one base and three bases was distinguished.

An exposure method using a VCSEL array of the present invention allow exposure to be conducted more conveniently and with a lower cost than a usual exposure method using a photomask or employing laser scanning. Furthermore, this invention provides a convenient method for preparing a solid-phase two-dimensional nucleic acid probe array.

What is claimed is:

1. A method for manufacturing a nucleic acid array where multiple nucleic acid strands attach to multiple positions on a substrate surface and each of the nucleic acid strands has an inherent base sequence, comprising the steps of:
   (a) preparing a substrate with the surface on which nucleic acid is bound at multiple positions, in which one end is bound to the substrate while the other end is protected with a photolytic protective group;
   (b) selectively irradiating given nucleic acids among the multiple nucleic acids bound to the substrate surface with laser light using an exposure device where multiple vertical cavity surface emitting laser sources are aligned as an array, wherein driving each of the multiple vertical cavity surface emitting laser sources for emitting laser light is controlled individually such that each said photolytic protective group of said given nucleic acids is irradiated with an emission laser beam from the laser sources to remove the photolytic protective group;
   (c) extending the nucleic acid strand by binding a given nucleotide having photolytic protective group according to the base sequence; and
   (d) repeating said (b) and (c) steps on the extended strands until the base sequence is completed.

2. A method for manufacturing peptide array where multiple peptide strands attach to multiple positions on a substrate surface and each of the peptide strands has an inherent sequence, comprising the steps of:
   (a) preparing a substrate with the surface on which a peptide is bound at multiple positions, in which one end is bound to the substrate while the other end is protected with a photolytic protective group;
   (b) selectively irradiating given peptides among the multiple peptides bound to the substrate surface with laser light using an exposure device where multiple vertical cavity surface emitting laser sources are aligned as an array, wherein driving each of the multiple vertical cavity surface emitting laser sources for emitting laser light is controlled individually such that each of said photolytic protective group of said given peptides is irradiated with an emission laser beam from the laser sources to remove the photolytic protective group;
   (c) extending the peptide strand by binding a given peptide having photolytic protective group according to the sequence; and
   (d) repeating said (b) and (c) steps on the extended peptide strands until the sequence is completed.

3. A method for forming a nucleic acid array wherein nucleic acid strands are bound to multiple positions of a substrate, comprising the steps of:
   (a) selectively irradiating photolytic protective groups on an end of the desired nucleic acids on the substrate with laser beams from multiple vertical cavity surface emitting laser sources to remove the photolytic protective groups, wherein each of the laser sources is individually controlled;
   (b) extending the desired nucleic acids with a desired nucleotide having a photolytic protective group; and
   (c) repeating steps (a), and (b) until the strands are completed.

* * * * *

SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Probe Sequence

<400> SEQUENCE: 1
actggccgtc   gttttaca                                           18

<210> SEQ ID NO 2
<211> LENGTH: 18
<212> TYPE: DNA
<213> ORGANISM: Artificial Sequence
<220> FEATURE:
<223> OTHER INFORMATION: Probe Sequence

<400> SEQUENCE: 2

-continued

```
actggccgtt   gttttaca                                             18

<210> SEQ ID NO 3
<211> LENGTH: 18
<212> TYPE: DNA
<213> ORGANISM: Artificial Sequence
<220> FEATURE:
<223> OTHER INFORMATION: Probe Sequence

<400> SEQUENCE: 3
actggccgtt   tttttaca                                             18

<210> SEQ ID NO 4
<211> LENGTH: 18
<212> TYPE: DNA
<213> ORGANISM: Artificial Sequence
<220> FEATURE:
<223> OTHER INFORMATION: Probe Sequence

<400> SEQUENCE: 4
actggcatct   tttttaca                                             18

<210> SEQ ID NO 5
<211> LENGTH: 18
<212> TYPE: DNA
<213> ORGANISM: Artificial Sequence
<220> FEATURE:
<223> OTHER INFORMATION: Probe Sequence

<400> SEQUENCE: 5
tataaaccga   cggccagt                                             18
```